United States Patent [19]

Chow et al.

[11] Patent Number: 4,668,672
[45] Date of Patent: May 26, 1987

[54] FEED COMPOSITIONS CONTAINING PYRIDYLALKYLHYDRAZIDES

[75] Inventors: Alfred W. Chow, Radnor; Thomas O. Lindsey, Coatesville, both of Pa.; Winfred J. Sanders, Mt. Laurel, N.J.

[73] Assignee: SmithKline Beckman Corporation, Philadelphia, Pa.

[21] Appl. No.: 710,790

[22] Filed: Mar. 12, 1985

[51] Int. Cl.$^4$ .................. A61K 31/55; A61K 31/445; A61K 31/44
[52] U.S. Cl. .................................. 514/212; 514/216; 514/318; 514/339; 514/357
[58] Field of Search ............... 514/318, 357, 339, 216, 514/318, 212

[56] References Cited

U.S. PATENT DOCUMENTS 4,317,776  3/1982  Klayman et al. ................ 260/244.4
4,385,055  5/1983  Klayman et al. ................ 424/248.4
4,493,930  1/1985  Klayman et al. .................. 544/360

OTHER PUBLICATIONS

D. L. Klayman et al., J. Med. Chem., 22, 855 and 1367 (1979).

Primary Examiner—Frederick E. Waddell
Attorney, Agent, or Firm—William H. Edgerton; Stuart R. Suter; Alan D. Lourie

[57] ABSTRACT

Selected pyridylalkylhydrazides are used as active ingredients in animal feed compositions and in methods for increasing the growth and feed efficiency of monogastric, meat-producing animals. A particularly useful active ingredient of this invention is 3-azabicyclo-[3.2.2]nonane-3-carbothioic acid 2-[1-(2-pyridyl)ethyl]-hydrazide.

5 Claims, No Drawings

FEED COMPOSITIONS CONTAINING PYRIDYLALKYLHYDRAZIDES

This invention comprises new animal feed compositions and methods using pyridylalkylhydrazides as active ingredients for altering metabolism in the digestive tract of monogastric, meat-producing animals, thereby improving growth and feed efficiency of the animals.

BACKGROUND OF THE INVENTION

Certain 2-acetylpyridinethiosemicarbazones have been described to have anti-malarial or anti-bacterial activity; U.S. Pat. Nos. 4,317,776, 4,493,930, and 4,385,055, J. Med. Chem. 22, 855 (1979), J. Med. Chem. 22, 1373 (1979). These references also describe the chemical preparation of certain important active ingredients of the present invention. The references do not disclose the use of the chemical compounds in animal feed compositions or their use to increase feed efficiency in meat-producing animals such as poultry. The useful quantities of the active ingredients in the present invention are lower than the anti-bacterial levels which are described as useful in the prior art.

DESCRIPTION OF THE INVENTION

The supplemented animal feed compositions of this invention are fed to monogastric, growing or fattening, meat-producing animals, especially to swine or poultry.

It is known to the art that, during assimilation of food, the production of volatile fatty acids and lactic acid in swine should be relatively low in the upper part of the digestive tract. On the other hand, glucose levels should be higher in the upper tract. Lysine is an essential amino acid which is necessary for growth. Therefore, high levels of lysine are also desirable. Often, corn diets, which are naturally low in lysine, are supplemented with lysine.

The active ingredients of this invention however do not improve feed efficiency by an effect on the volatile fatty acids directly but by another mechanism of action, possibly by means of inhibiting anaerobic bacteria in the digestive tract. Therefore, this invention enables the grower to obtain a larger than normal amount of energy and amino acid equivalent available to his animals for growth from each unit of food in their diets.

The active ingredients, which are useful in the feed compositions and methods of this invention, are illustrated by the structural formula:

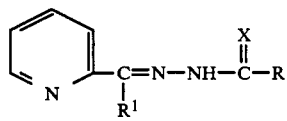

(I)

in which:
R is $C_{1-6}$-alkylthio, hydrogen, $C_{1-6}$-alkoxy, N-piperazinyl, N-homopiperazinyl, N-$C_{4-7}$-alkyleneimino which is optionally C,C-bridged with an alkylene, especially an ethylene or propylene, when possible, amino, $C_{1-6}$-alkylamino or di-$C_{1-6}$-alkylamino;

X is S or O; and
$R^1$ is hydrogen, methyl or ethyl.

A subgeneric group of active ingredients are those of formula I in which:
R is N-azabicyclo[3.2.2]nonane or N-hexahydro-1H-azepine;
X is S, and
$R^1$ is methyl.

Also included as active ingredients are the nontoxic, acid addition salts of the compounds of formula I whenever they can be formed as will be apparent to those skilled in the art. Such salts are the hydrochloride or hydrobromide salts. Usually, the free base forms of the active ingredients are used.

The active ingredients of formula I are known compounds as discussed above and are prepared as taught by the referenced publications. Among the preferred ingredients are the compounds of formula I which are specifically disclosed in the Journal of Medicinal Chemistry 22, 1369–1371 (1979) in Table 1.

The feed compositions of this invention comprise the normal feed rations of meat-producing animals which are supplemented by a quantity of an active ingredient of formula I, which is effective for improving the growth rate or feed efficiency of the animals but which is not toxic or noxious to a degree that the animals will reduce ingestion of the ration. The quantity of the active ingredient will vary, as is known to the art, with factors such as the cost of the ingredient, the species and the size of animal, the relative activity of the compound of formula I or the type of feed ration used as the basal feed.

Representative feed rations for swine and poultry are in the examples presented hereafter. Swine feed from weanling to fattening or finishing rations may be supplemented. Swine eat from about 0.9 kg per day (for a 11 kg pig) to 4 kg per day (for a 66 kg pig). Most rations are comprised of a corn base supplemented with legume silage, wheat bran, oats, barley, molasses or a protein supplement.

Poultry feeds comprise starter rations, broiler rations and laying rations. The rations are usually based on ground corn, corn meal and soybean meal. The broiler rations also often contain high energy supplements such as added fats, proteins and vitamins. Turkey rations are similar, but comprise only a starting ration and a growing ration. Chickens or pheasants eat from 12–120 grams of feed per day, turkeys twice that much. Estimated intake of feed is dependent on the weight and age of the meat producing animal. Usually, rye-based feeds are most useful as carriers for the active ingredients of this invention.

A selected active ingredient of formula I is mixed uniformly with the described feed rations to give a supplemented ration which is, then, fed as to custom. This is, most often, ad libitum. Conveniently, a premix of the supplemental growth promotant of this invention, which is optionally combined with or without other supplements known to this art such as an anthelmintic, a nitrogen source or an antibiotic such as virginiamycin or oxytetracycline, is prepared by the manufacturer for sale to the formulators or feed lot operators. The concentration of hydrazide in the premix is usually from 5–75% by weight or a concentration 100–2000 times greater than that in the complete feed ration. The premix form may be liquid or solid. Premix vehicles are corn oil, cottonseed oil, molasses or distillers solubles to form a liquid premix preparation. sucrose, lactose, corn meal, ground corn, flour, calcium carbonate or soybean meal are often used as bases for solid premix preparations. The premix composition is, then, mixed uniformly with whole ration which is commonly fed to the target animal. Such premix compositions are included in the term "feed compositions" as used herein.

The concentration of the hydrazide of formula I in the complete ration is a nontoxic but active quantity chosen, for example, from a range of about 1–100 parts of active ingredient by weight per million parts of whole feed (ppm) or about 1.1–110 grams per ton. Advantageously, a quantity is chosen from the range of 5–50 ppm of a hydrazide of formula I.

The percentage ratio by weight of active ingredient to feed suggested for this invention is selected from the range of about 0.0001–0.01% which is lower than the effective range for biological activity described in the referenced publications.

The method of this invention comprises feeding to growing, monogastric, meat-producing animals, especially swine and poultry, an effective growth-promoting but nontoxic quantity of a compound of formula I. Other monogastric animals whose digestive tract features fermentation in a cecum or cecum-like chamber are rabbits and horses.

The supplemented feed rations described above are presented to the animal by methods known to the art. Ad libitum feeding in the pasture, pen or growing shed is most convenient to increase the growth rate of the animal and to increase the feed efficiency of the growing operation. Alternatively, the same supplemented feeds may be given to ruminant animals, particularly when the compound of formula I is coated to bypass the upper stomach or rumen.

For example, species of the active ingredients of this invention, such as 3-azabicyclo[3.2.2]nonane-3-carbothioic acid 2-[1-(2-pyridyl)ethyl]hydrazide at 50 ppm or hexahydro-1H-azepine-1-carbothioic acid [1-(2-pyridinyl)-ethylidinyl]hydrazide at 10 and 50 ppm, fed to chickens produced increased weight gain and better feed conversion. Concentrations of these species in whole feed ration which have proved effective are about 5–50 ppm.

The following working examples are intended to illustrate this invention. All percentages are by weight. All temperatures are Centigrade.

EXAMPLE 1

A swine ration for growing hogs of 18–45 kilograms of body weight is prepared using the following formula:

| | |
|---|---|
| Corn, ground | 78.15% |
| Soybean oil meal, 44% | 17.0% |
| Meat scraps, 50% | 3.0% |
| Oyster shell flavor | 0.4% |

-continued

| | |
|---|---|
| Bone meal | 0.5% |
| Zinc oxide | 0.01% |
| Vitamin A, B, $B_{12}$ and D supplement | optional |

The ration is supplemented to 100% with 20 ppm of 3-azabicyclo[3.2.2]nonane-3-carbothioic acid 2-[1-(2-pyridyl)ethyl]hydrazide distributed through a premix carrier. The ration is fed, ad libitum, to the penned growing or fattening swine.

EXAMPLE 2

A chicken ration for broilers is prepared using the following formula:

| | |
|---|---|
| Yellow corn meal | 67.35% |
| Soybean oil meal | 24.00% |
| Menhaden fish meal | 6.00% |
| Steamed bone meal | 1.00% |
| Ground limestone | 1.00% |
| Iodized salt | 0.34% |
| 25% choline chloride | 0.13% |
| Vitamin $B_{12}$ | 0.10% |
| Manganese sulfate | 0.02% |
| Vitamin mix | 0.06% |

The ration is supplemented with 20 ppm of hexahydro-1H-azepine-1-carbothioic acid [1-(2-pyridyl)-ethylidinyl]hydrazide in a premix and is then fed ad libitum to the chicks.

EXAMPLE 3

In Vitro Swine Procedure

A. Methodology:

A Yorksire barrow is surgically prepared either with an ileal cannula, which is placed 15 cm. from the ileo-ceco-colic junction, or a cecal cannula, which is placed midway between the apex and origin of the cecum. The animal is fed 4 times daily to restrict intake to 4.5% of body weight in a 30 kg animal or 2.5% of body weight in a 100 kg animal. The swine grower ration is:

| | % w/w |
|---|---|
| Medium ground shelled corn | 70.60 |
| Soybean meal, 44% | 22.00 |
| Dehydrated alfalfa meal, 17% | 4.50 |
| Calcium propionate | 0.15 |
| Vitamin/mineral premix | 2.75 |

Sampling of the material, via the cannula, begins 150–180 minutes following the first morning feeding and continues any time from 30–120 minutes thereafter, depending on the quantity of material needed. The sample is maintained in crushed ice, no cooler than 5°, and is gassed continuously with carbon dioxide. The collected material is filtered. The filtrate is the inoculum used for incubations of the test and control samples. The gassed inoculum, 2.25 ml, is placed in each of 10 gassed test tubes, each containing 0.75 ml of a nutrient solution and 0.5 mg of each test compound. Four blank control tubes, along with the test compound tubes, are incubated 5 hours at 37° with agitation. Four more killed tubes are included which are not incubated.

The tubes are each treated with 0.60 ml of a 25% solution of metaphosphoric acid, then, stored at −4° until analysis. Samples are thawed and centrifuged for 25 minutes at 20,000 r.p.m. The supernatent liquid is decanted, sampled for gas chromatography and automatic analyzing. The results are fed into a computer for finishing to give figures in which the blank control value is 100%. Virginiamycin is used as a positive control.

B. Results:

| Compound | % of Control Values | | | |
|---|---|---|---|---|
| | VFA | LYS | GLU | LAC* |
| Virginiamycin 116.67 ppm | 25 | 171 | 190 | 17 |

1.

$$\text{Pyridine-}C(CH_3)=N-NH-C(=S)-N\text{(piperidine)}$$

| 166.67 ppm | 63 | 23 | 100 | 104 |
| 166.67 ppm | 103 | 18 | 102 | 99 |

2.

$$\text{Pyridine-}C(CH_3)=N-NH-C(=O)-O-CH_3$$

| 166.67 ppm | 88 | 99 | 114 | 104 |
| 16.67 ppm | 94 | 134 | 117 | 107 |
| 1.67 ppm | 104 | 70 | 83 | 95 |

3.

$$\text{Pyridine-}C(H)=N-NH-C(=O)-O-CH_3$$

| 166.67 ppm | 109 | 109 | 92 | 99 |
| 16.67 ppm | 104 | 140 | 114 | 106 |
| 1.67 ppm | 90 | 65 | 99 | 96 |

4.

$$\text{Pyridine-}C(CH_3)=N-NH-C(=S)-NH_2$$

| 166.67 ppm | 43 | 137 | 147 | 88 |

5.

$$\text{Pyridine-}C(CH_3)=N-NH-C(=S)-N\text{(cycloalkyl)}$$

| 166.67 ppm | 97 | 107 | 99 | 102 |

6.

$$\text{Pyridine-}C(CH_3)=N-NH-C(=S)-SCH_3$$

| 166.67 ppm | 89 | 103 | 95 | 113 |

*VFA refers to the total of volatile fatty acids, namely acetate, propionate, isobutyrate, butyrate, isovalerate and valerate. LYS is lysine, GLU is glucose and LAC is L-lactic acid.

One skilled in the art will note that the results from testing representative active ingredients of this invention in the in vitro fistula procedure indicate little change in the fatty acid profile in the digestive tract. This, taken together with the positive results in vivo presented in the next example, may indicate the growth activity is due to activity against anaerobic bacteria in the tract.

EXAMPLE 4

Chick Growth Study

A. Methodology:

512 Day old broiler chicks, selected for weight, health and sex, are housed in an environmentally controlled room with temperature at 37.7° and humidity at 40%. Chicks are fed ad libitum. Water is offered ad libitum. A corn or, preferably, rye basal ration is fed during the acclimation period (days 1 and 2), then, mixed with the compound under test or used as a control on days 3–17. Either 8 or 16 chicks are used for each test or control group.

| Basal Rye Diet | |
|---|---|
| Diet Ingredients | (% w/w) |
| Ground Rye (fine grind) | 54.6 |
| Soybean Meal (49% protein) | 27 |
| Meat & Bone meal (50% protein) | 10 |
| Dehydrated Alfalfa meal | 1.25 |
| Fat, Animal | 4 |
| Dried Whey (or lactose) | 1 |
| Ground Limestone | 0.67 |
| Dicalcium Phosphate | 0.50 |
| Iodized salt | 0.23 |
| Vitamin premix | 0.175 |
| Trace Mineral premix | 0.25 |
| DL methionine (98%) | 0.25 |
| Choline Chloride (50% aqueous sol.) | 0.150* |

*Since choline is added as a 50% aqueous solution, its percentage in diet is doubled.

B. Results:

| | % of Control | |
|---|---|---|
| Chemical | Weight (17 day) | Feed Gain (3–17 day) |
| Virginiamycin 50.0 | 118.9 | 85.0 |

1.

$$\text{Pyridine-}C(CH_3)=N-NH-C(=S)-N\text{(piperidine)}$$

| 50 ppm | 102.8 | 80.6 |
| 50 ppm | 115.3 | 84.4 |
| 50 ppm | 109.1 | 83.3 |

2.

$$\text{Pyridine-}C(CH_3)=N-NH-C(=S)-N\text{(piperidine)}$$

| 50 ppm | 102.8 | 80.6 |
| 10 ppm | 109.5 | 92.3 |

-continued

| | | % of Control | |
|---|---|---|---|
| Chemical | | Weight (17 day) | Feed Gain (3-17 day) |
| 3. | pyridine-C(=N-NH-C(=O)-OCH$_3$)-H (4-pyridyl) | | |
| | 40 ppm | 96.9 | 102.5 |
| 4. | pyridine-C(=N-NH-C(=O)-OCH$_3$)-H (3-pyridyl) | | |
| | 50 ppm | 98.4 | 101.7 |
| 5. | pyridine-C(=N-NH-C(=O)-OCH$_3$)-H (2-pyridyl) | | |
| | 50 ppm | 118.6 | 86.4 |
| | 50 ppm | 103.4 | 99.2 |
| | 50 ppm | 103.0 | 97.9 |
| 6. | pyridine-C(=N-NH-C(=O)-OCH$_3$)(CH$_3$) | | |
| | 50 ppm | 110.1 | 94.0 |
| | 50 ppm | 105.8 | 96.9 |
| | 50 ppm | 102.6 | 99.8 |
| 7. | pyridine-C(=NNH-C(=S)-NH$_2$)(CH$_3$) | | |
| | 50 ppm | 106.6 | 91.2 |
| 8. | pyridine-C(=N-NH-C(=S)-N<ring>)(CH$_3$) | | |
| | 49 ppm | 102.0 | 84.1 |

-continued

| | | % of Control | |
|---|---|---|---|
| Chemical | | Weight (17 day) | Feed Gain (3-17 day) |
| 9. | pyridine-C(=N-NH-C(=S)-SCH$_3$)(CH$_3$) | | |
| | 40 ppm | 72.8 | 86.6 |
| 10. | 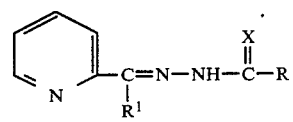 | | |
| | 10 ppm | 109.5 | 92.3 |
| | 50 ppm | 102.8 | 80.6 |

The data above demonstrate the utility of this invention. Comparison of the activity of isomeric compounds 2, 3 and 4 demonstrates the unexpected activity of the active ingredients of formula I.

What is claimed is:

1. The method of improving the weight gain or feed efficiency of meat-producing monogastric animals comprising feeding to said animals an effective but nontoxic quantity of a compound of the formula:

$$\text{pyridine-C(=N-NH-C(=X)-R)(R}^1\text{)}$$

in which:

R is $C_{1-6}$-alkylthio, hydrogen, $C_{1-6}$-alkoxy, N-piperazinyl, N-homopiperazinyl, N-$C_{4-7}$-alkyleneimino which is optionally C,C-bridged with ethylene or propylene, amino, $C_{1-6}$-alkylamino or di-$C_{1-6}$-alkylamino;

X is S or O; and $R^1$ is hydrogen, methyl or ethyl, or a nontoxic, stable acid addition salt thereof.

2. The method of claim 1 in which the compound is fed in the form of an animal feed ration containing from about 1 to about 100 parts of compound per million parts of ration by weight.

3. The method of claim 1 in which R is N-3-azabicyclo[3.2.2]nonane.

4. The method of claim 1 in which R is N-hexahydro-1H-azepine.

5. The method of claim 2 in which the ration contains from about 5 to about 50 parts of compound per million parts of ration by weight.

* * * * *